(12) United States Patent
Lawyer

(10) Patent No.: US 6,423,719 B1
(45) Date of Patent: Jul. 23, 2002

(54) METHOD FOR TREATING BENIGN PROSTATE HYPERPLASIA

(75) Inventor: Carl H. Lawyer, Mequon, WI (US)

(73) Assignee: Upsher-Smith Laboratories, Inc., Minneapolis, MN (US)

( * ) Notice: Subject to any disclaimer, the term of this patent is extended or adjusted under 35 U.S.C. 154(b) by 0 days.

(21) Appl. No.: 09/505,220

(22) Filed: Feb. 16, 2000

Related U.S. Application Data
(60) Provisional application No. 60/120,099, filed on Feb. 16, 1999.

(51) Int. Cl.$^7$ .............................................. A61K 31/52

(52) U.S. Cl. ............................ 514/263; 514/8; 514/12; 514/15; 514/264; 514/265; 514/922

(58) Field of Search ............................... 514/8, 12, 15, 514/263, 264, 265, 922

(56) References Cited

U.S. PATENT DOCUMENTS

| | | | |
|---|---|---|---|
| 2,575,344 | A | 11/1951 | Jones et al. |
| 4,031,218 | A | 6/1977 | El-Antably |
| 4,187,308 | A | 2/1980 | Franzone et al. |
| 4,341,783 | A | 7/1982 | Scheindlin |
| 4,581,359 | A | 4/1986 | Ayres |
| 5,171,217 | A | * 12/1992 | March et al. .................. 604/53 |
| 5,753,641 | A | 5/1998 | Gormley et al. |
| 5,891,904 | A | 4/1999 | Stief et al. |

OTHER PUBLICATIONS

Chemical Abstracts 121:50051, "Ocular hypotension induced by topical dopaminergic drugs and phosdiesterase inhibitors" (1994).*

Kukovetz et al., "Overadditive Synergism Between Theophylline, Diprophylline and Proxyphylline in Tracheal Smooth Muscle Relaxation," *Arzneimittelforschung*, 33(10):1450–1454 (1983).

Brambilla et al., "Activation of the $A_3$ adenosine receptor affects cell cycle progression and cell growth," *Naunyn-Schmiedeberg's Arch Pharmacol*, 2000 Mar.; 361(3):225–34.

Brodie et al., "Activation of the $A_{2A}$ adenosine receptor inhibits nitric oxide production in glial cells," *FEBS Lett.* 1998 Jun.; 429(1):139–42.

Conti et al., "The Molecular Biology of Cyclic Nucleotide Phosphodiesterases," *Prog Nucleic Acid Res Mol Biol.* 1999;63:1–38.

Conti, "Phosphodiesterases and cyclic nucleotide signaling in endocrine cells," *Mol Endocrinol.* 2000 Sep.;14(9):1317–27.

Granovsky et al., "Identification of the gamma subunit–interacting residues on photoreceptor cGMP phosphodiesterase, PDE6α'," *J Biol Chem.* 2000 Dec. 29;275(52):41258–62.

Hasan et al., "Antagonism of coronary artery relaxation by adenosine $A_{2A}$–receptor antagonist ZM241385," *J Cardiovasc Pharmacol.* 2000 Feb.; 35(2):322–5.

Kotera et al., "Immunohistochemical localization of cGMP–binding cGMP–specific phosphodiesterase (PDE5) in rat tissues," *J Histochem Cytochem.* 2000 May;48(5):685–93.

Landells et al., "The role of adenosine receptors in the action of theophylline on human peripheral blood mononuclear cells from healthy and asthmatic subjects," *Br J Pharmacol,* 2000 Mar.; 129(6):1140–4.

Lew et al., "Examination of adenosine receptor–mediated relaxation of the pig coronary artery," *Clin Exp Pharmacol Physiol,* 1999 May–Jun.; 26(5–6):438–43.*

Li et al., "Adenosine $A_{2a}$ receptors increase arterial endothelial cell nitric oxide," *J Surg Res,* 1998 Dec.; 80(2):357–64.*

Li et al., "Adenosine enhances nitric oxide production by vascular endothelial cells," *Am J Physiol,* 1995 Aug.; 269(2 Pt 1):C519–23.*

Olanrewaju et al., "Adenosine $A_{2A}$ and $A_{2B}$ receptors in cultured human and porcine coronary artery endothelial cells," *Am J Physiol Heart Circ Physiol,* 2000 Aug.; 279(2):H650–6.*

Rump et al., "Adenosine mediates nitric–oxide–independent renal vasodilation by activation of $A_{2A}$ receptors," *J Hypertens.* 1999 Dec.; 17(12 Pt 2):1987–93.*

Schmeichel et al., "Methylxanthine bronchodilators potentiate multiple human neutrophil functions," *J Immunol.* 1987 Mar.; 138(6):1896–903.*

Schmidt et al. "The Effect of Selective and Non–selective Phosphodiesterase Inhibitors on Allergen– and Leukotriene C(4)–Induced Contractions in Passively Sensitized Human Airways," *Br J Pharmacol.* 2000 Dec.;131(8):1607–18.*

Shneyvays et al., "Induction of apoptosis in cardiac myocytes by an $A_3$ adenosine receptor agonist," *Exp Cell Res.* 1998 Sep.; 243(2):383–97.*

Shneyvays et al., "Induction of apoptosis in rat cardiocytes by $A_3$ adenosine receptor activation and its suppression by isoproterenol," *Exp Cell Res.* 2000 May; 257(1):111–26.*

(List continued on next page.)

Primary Examiner—Frederick Krass
(74) Attorney, Agent, or Firm—Mueting, Raasch & Gebhardt, P.A.

(57) ABSTRACT

A method of treating and/or preventing renal dysfunction in a patient, such as renal colic or contrast nephropathy by administering to a patient, a compound of the formula:

is described herein. Administration of dyphylline in a sustained release oral dosage form is preferred.

21 Claims, No Drawings

OTHER PUBLICATIONS

This Week in Science: from *Science.* Jun. 9, 2000; 288(5472):1701.*

Walker et al., "Adenosine $A_{2a}$ receptor activation delays apoptosis in human neutrophils," *J Immunol,* 1997 Mar.; 158(6):2926–31.*

Xu et al., "Atomic Structure of PDE4: Insights into Phosphodiesterase Mechanism and Specificity," *Science.* Jun. 9, 2000; 288:822–1825.*

Yasui et al., "Effects of theophylline on human eosinophil functions: comparative study with neutrophil functions," *J Leukoc Biol.* 2000 Aug.; 68(2):194–200.*

Yasui et al., "Theophylline induces neutrophil apoptosis through adenosine $A_{2A}$ receptor antagonism," *J Leukoc Biol.* 2000 Apr.; 67(4):529–35.*

Andersson, "The Concept of Uroselectivity," *Eur. Urol.,* 33(Suppl. 2):7–11 (1998).

Bang et al., "Cyclic AMP induces transforming growth factor β2 gene expression and growth arrest in the human androgen–independent prostate carcinoma cell line PC–3," *Proc. Natl. Acad. Sci. USA,* 89(8):3556–3560 (1992).

Barza, "Anatomical Barriers for Antimicrobial Agents," *Eur. J. Clin. Microbiol. Infect. Dis.,* 12(Suppl. 1):S31–S35 (1993).

Boatman et al., "Pharmacological Evaluation of Ureteral Smooth Muscle, A Technique for Monitoring Ureteral Peristalsis," *Invest. Urol.,* 4(6):509–520 (1967).

Coe et al., "The Pathogenesis and Treatment of Kidney Stones," *N. Engl. J. Med.,* 327(16):1141–1152 (1992).

Edelstein et al., "Chapter 8: Etiology, Pathogenesis, and Management of Renal Failure," *Campbell's Urology, 7th edition,* Walsh et al., eds., W.B. Saunders Co., Philadelphia, Title page, publication page, table of contents, and pp. 315–341 (1998).

Fair et al., "The pH of Prostatic Fluid: A Reappraisal and Therapeutic Implications," *J. Urol.,* 120(6):695–698 (1978).

Fang et al., "$P_2$—Purinergic Receptor Agonists Inhibit the Growth of Androgen–independent Prostate Carcinoma Cells," *J. Clin. Invest.,* 89(1):191–196 (1992).

Kawabe et al., "Use of an α1–Blocker, YM617, in the Treatment of Benign Prostatic Hypertrophy," *J. Urol.,* 144(4):908–912 (1990).

Kerttula et al., "Theophylline infusion modulates prostaglandin and leukotriene production in man," *Prostaglandins Leukot. Essent. Fatty Acids,* 57(6):555–560 (1997).

Leoni et al., "the Effects of Isoproterenol and Aminophylline on Detrusor Muscle Contractility in an Organ Bath Apparatus," *Invest. Urol.,* 10(6):458–463 (1973).

Martin et al., "Relationship Between the Effects of Alfuzosin on Rat Urethral and Blood Pressures and its Tissue Concentrations," *Life Sci.,* 63(3):169–176 (1998).

Martin et al., "Functional Uroselectivity," *Eur. Urol.,* 33(Suppl. 2):12–18 (1998).

Nadai et al., "Pharmacokinetics and the Effect of Probenecid on the Renal Excretion Mechanism of Diprophylline," *J. Pharm. Sci.,* 81(10):1024–1027 (1992).

Oesterling, "Benign Prostatic Hyperplasia—Medical and Minimally Invasive Treatment Options," *N. Engl. J. Med.,* 332(2):99–109 (1995).

Simons et al., "Urinary Excretion of Dyphylline in Humans," *J. Pharm. Sci.,* 68(10):1327–1329 (1979).

Wein et al., "The Effects of Aminophylline on Ureteral and Bladder Contractility," *Invest. Urol.,* 9(4):290–293 (1972).

Acara et al., "Probenecid inhibition of the renal excretion of dyphylline in chicken, rat and man," *J. Pharm. Pharmacol.,* 39(7):526–530 (1987).

Becker et al., "The effect of the specific phosphodiesterase–IV–inhibitor rolipram on the ureteral peristalsis of the rabbit in vitro and in vivo," *J. Urol.,* 160(3Pt.1):920–925 (1998).

Drescher et al., "Alpha–1 receptor mediated smooth muscle regulation in benign prostatic hyperplasia," *Scand. J. Urol. Nephrol. Suppl.,* 157:33–40 (1994).

Drescher et al., "Smooth Muscle Contractility in Prostatic Hyperplasia: Role of Cyclic Adenosine Monophosphate," *Prostate,* 25(2):76–80 (1994).

Drescher et al., letter to Editor (regarding "Nephrotoxicity from contrast media: attenuation with theophylline," which appeared in *Radiology,* 195(1):17–22 (1995)), *Radiology,* 197(2):547–548 (1995).

Drescher, "$Ca^{2+}$ and Cyclic Adenosine Monophosphate Involvement in Radiographic Contrast Medium–induced Renal Vasoconstriction," *J. Vasc. Interv. Radiol.,* 6(5):813–818 (1995).

Erley et al., "Adenosine antagonist theophylline prevents the reduction of glomerular filtration rate after contrast media application," *Kidney Int.,* 45(5):1425–1431 (1994).

Gladstone et al., "The use of theophylline ethylene diamine (aminophylline) for the relief of biliary colic: a preliminary report," *J. Am. Med. Assoc.,* 126(17):1084–1085 (1944).

Katholi et al., "Nephrotoxicity from Contrast Media: Attenuation with Theophylline," *Radiology,* 195(1):17–22 (1995).

King et al., "Purinergic Modulation of Rat Urinary Bladder Detrusor Smooth Muscle," *Gen. Pharmacol.,* 29(4):597–604 (1997).

Kolonko et al., "The nonselective adenosine antagonist theophylline does prevent renal dysfunction induced by radiographic contrast agents," *J. Nephrology,* 11(3):151–156 (1998).

Lawyer et al., "Utilization of intravenous dihydroxypropyl theophylline (dyphylline) in an aminophylline–sensitive patient, and its pharmacokinetic comparison with theophylline," *J. Allergy Clin. Immunol.,* 65(5):353–357 (1980).

May et al., "Effect of probenecid on dyphylline elimination," *Clin. Pharmacol Therapeut.,* 33(6):822–825 (1983).

Morcos et al., "Nephrotoxicity from Contrast Media: Attenuation with Theophylline," letter to Editor (regarding "Nephrotoxicity from contrast media: attenuation with theophylline," which appeared in *Radiology,* 195(1):17–22 (1995)), *Radiology,* 197(2):546–547 (1995).

Morcos et al., "Contrast Media–induced Nephrotoxicity: A New Insight," *Clin. Radiol.,* 52(8):573–574 (1997).

Nolan, "Theophylline option for attenuating contrast media–induced nephrotoxicity in patients on metformin," *Am. J. Health–Syst. Pharm.,* 54(5):587–588 (1997).

Osswald et al., "Therapeutic use of theophylline to antagonize renal effects of adenosine," *Clin. Nephrol.,* 43(Suppl. 1):S33–S37 (1995).

Quasny, "Metformin, contrast media, and theophylline," *Am. J. Health–Syst. Pharm.,* 54(17):2007–2008 (1997).

* cited by examiner

METHOD FOR TREATING BENIGN PROSTATE HYPERPLASIA

CROSS-REFERENCE TO RELATED APPLICATION

This application claims the benefit of a provisional application filed Feb. 16, 1999, entitled "Method for Treating Benign Prostate Hyperplasia," and having Ser. No. 60/120,099, which is incorporated herein by reference.

FIELD OF INVENTION

The present invention relates to a method of treating benign prostate hyperplasia in a subject suffering therefrom with an effective amount of dyphylline or an analog thereof.

BACKGROUND

Xanthine is a dioxypurine that is structurally related to uric acid. Xanthine can be represented by the following structure:

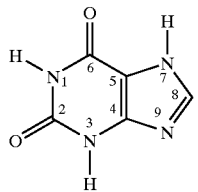

Caffeine, theophylline and theobromine are methylated xanthines. Methylated xanthines such as caffeine and theophylline are typically used for their bronchodilating action in the management of obstructive airways diseases such as asthma. The bronchodilator effects of methylxanthines are thought to be mediated by relaxation of airway smooth muscle. Generally, methylxanthines function by inhibiting cyclic nucleotide phosphodiesterases and antagonizing receptor-mediated actions of adenosine.

Theophylline can be represented by the following structure:

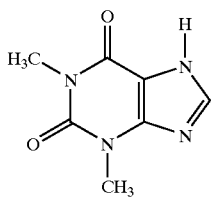

However, when administered intravenously or orally, theophylline has numerous undesired or adverse effects that are generally systemic in nature. It has a number of adverse side effects, particularly gastrointestinal disturbances and CNS stimulation. Nausea and vomiting are the most common symptoms of theophylline toxicity. Moderate toxicity is due to relative epinephrine excess, and includes tachycardia, arrhythmias, tremors, and agitation. Severe toxicity results in hallucinations, seizures, dysrhythmias and hypotension. The spectrum of theophylline toxicity can also include death.

Furthermore, theophylline has a narrow therapeutic range of serum concentrations above which serious side effects can occur. The pharmacokinetic profile of theophylline is dependent on liver metabolism, which can be affected by various factors including smoking, age, disease, diet, and drug interactions.

Generally, the solubility of methylxanthines is low and is enhanced by the formation of complexes, such as that between theophylline and ethylenediamine (to form aminophylline). The formation of complex double salts (such as caffeine and sodium benzoate) or true salts (such as choline theophyllinate) also enhances aqueous solubility. These salts or complexes dissociate to yield the parent methylxanthine when dissolved in aqueous solution. Although salts such as aminophylline have improved solubility over theophylline, they dissociate in solution to form theophylline and hence have similar toxicities.

Dyphylline is a covalently modified derivative of xanthine (1,3,-dimethyl-7-(2,3-dihydroxypropl)xanthine. Because it is covalently modified, dyphylline is not converted to free theophylline in vivo. Instead, it is absorbed rapidly in therapeutically active form. Dyphylline has a lower toxicity than theophylline. Dyphylline can be represented by the following structure:

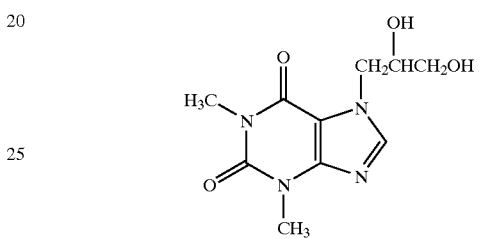

Dyphylline is an effective bronchodilator that is available in oral and intramuscular preparations. Generally, dyphylline possesses less of the toxic side effects associated with theophylline.

U.S. Pat. No. 4,031,218 (E1-Antably) discloses the use of 7-(2,3-dihydroxypropyl)-1,3-di-n-propylxanthine, a derivative of theophylline, as a bronchodilator. U.S. Pat. No. 4,341,783 (Scheindlin) discloses the use of dyphylline in the treatment of psoriasis and other diseases of the skin by topical administration of dyphylline. U.S. Pat. No. 4,581,359 (Ayres) discloses methods for the management of bronchopulmonary insufficiency by administering an N-7-substituted derivative of theophylline, including dyphylline, etophylline, and proxyphylline.

Benign prostatic hyperplasia (BPH) is a nonmalignant enlargement of the prostate that is due to excessive cellular growth of both glandular and stromal elements of the prostate. The condition is very common in men over 40 years of age. BPH has two components: a static component that is related to the enlargement of the prostate and a dynamic component that reflects the tone or degree of contraction of smooth muscle within the prostate. The smooth muscle tone depends on extra-and intracellular $Ca_{2+}$ stores and is regulated by various second messenger pathways, including cyclic 3'–5'adenosine monophosphate (cAMP).

Transurethral resection of the prostate is a common form of treatment. However, complications of transurethral resection include retrograde ejaculation, impotence, postoperative urinary tract infection and some urinary incontinence. Therefore, medical and/or minimally invasive treatments for benign prostatic hyperplasia are more desirable.

Minimally invasive treatments for BPH include transurethral incision of the prostate, balloon dilation of the prostate, prostatic stents, microwave therapy, laser prostatectomy, transrectal high-intensity focused ultrasound therapy and transurethral needle ablation of the prostate.

Known medical treatments for BPH include androgen deprivation therapy, the use of 5α-reductase inhibitors and α-adrenergic-antagonist drugs. Androgen deprivation therapy includes administering agents which diminish androgen secretion or action, such as gonadotrophin-releasing hormone (GnRH) analogues, antiandrogens. 5α-reductase inhibitors inhibit the action of type 2 5α-reductase, an enzyme that catalyzes the conversion of testosterone to dihydrotestosterone in most androgen sensitive tissues. Finasteride [N-(2-methyl-2-propyl)3-oxo-4-aza-5α-androst-1-ene-17β-carboxamide] is a known 5α-reductase inhibitor. α-Adrenergic antagonist drugs block adrenergic receptors in hyperplastic prostatic tissue, the prostatic capsule, and the bladder neck, to decrease smooth muscle tone of these structures. α-Adrenergic receptors in the trigone muscle of the bladder and urethra contribute to the resistance of outflow of urine. When smooth muscle tone is decreased, resistance to urinary flow through the bladder neck and the prostatic urethra decreases and urinary flow increases. A variety of α-adrenergic antagonists are used in the treatment of BPH. Nonselective drugs include phenoxybenzamine and thymoxamine. Short acting selective drugs include alfuzosin, indoramin and prazosin. Long acting selective drugs including doxazosin, terazosin and tamsulosin.

U.S. Pat. No. 5,753,641 (Gormley et al.) discloses a method for treating benign prostatic hyperplasia (BPH) involving combination therapy of a 5α-reductase inhibitor in combination with an $α_1$-adrenergic receptor blocker.

SUMMARY

The invention provides a method of treating benign prostatic hyperplasia or reducing the symptoms of benign prostatic hyperplasia by administering a therapeutic or prophylactic effective amount of dyphylline or a dyphylline analog, or a pharmaceutically acceptable salt thereof to the patient. According to the invention, the compound can be of the formula:

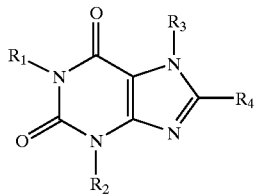

wherein $R_1$ and $R_2$, independently, are hydrogen or a $C_1–C_6$ linear or branched alkyl optionally interrupted by a carbonyl group. $R_3$ is a $C_1–C_8$ alkyl substituted by one or more moieties selected from the group consisting of a hydroxyl, amino, mercapto, dioxolan, carbonyl, and mixtures thereof. $R_4$ is hydrogen; a substituted or unsubstituted aromatic member selected from the group consisting of phenyl, biphenyl, benzyl, or furyl, in which the substituent is selected from the group consisting of $C_1–C_4$ alkyl, $C_1–C_4$ haloalkyl, $C_1–C_4$ alkoxy, $C_1–C_4$ alkylthio, halo and nitro; or cyclohexyl and cyclopentyl. Preferably, $R_1$ and $R_2$, are methyl; $R_3$ is dihydroxypropyl; and $R_4$ is hydrogen or a substituted or unsubstituted aromatic member selected from the group consisting of phenyl, biphenyl, benzyl, or furyl, in which the substituent is selected from the group consisting of $C_1–C_4$ alkyl, $C_1–C_4$ haloalkyl, $C_1–C_4$ alkoxy, $C_1–C_4$ alkylthio, halo and nitro. Most preferred is dyphylline, wherein $R_1$ and $R_2$ are methyl; $R_3$ is 2,3-dihydroxypropyl; and $R_4$ is hydrogen.

A second aspect of the present invention is a method of treating benign prostatic hyperplasia, or reducing the symptoms thereof, by administering a dyphylline-type compound, described above, with a combination of an α-adrenergic antagonist, such as phenoxybenzamine, thymoxamine, alfuzosin, indoramin, prazosin, doxazosin, terazosin and tamsulosin and/or a 5α-reductase inhibitor such as finasteride.

A third aspect of the present invention includes pharmaceutical compositions containing a dyphylline-type compound and an α-adrenergic antagonist and/or a 5α-reductase inhibitor. α-Adrenergic antagonists include nonselective drugs such as phenoxybenzamine and thymoxamine; short acting selective drugs such as alfuzosin, indoramin and prazosin; and long acting selective drugs such as doxazosin, terazosin and tamsulosin. Finasteride is an example of a 5α-reductase inhibitor. For a composition which includes a dyphylline-type compound and a nonselective α-adrenergic antagonist, a short acting selective α-adrenergic antagonist, or a 5α-reductase inhibitor, it is preferred that the entire composition be prepared in a sustained release formulation. However, in a composition which includes a dyphylline-type compound and a long-acting α-adrenergic antagonist, it is preferred that the dyphylline-type compound be prepared in a sustained release formulation and the long-acting α-adrenergic antagonist be prepared in a quick release formulation.

DETAILED DESCRIPTION

The invention is directed towards a method of treatment of benign prostatic hyperplasia by administering an effective amount of a dyphylline-type compound.

Dyphylline-type Compounds

According to the invention, a dyphylline-type compound includes dyphylline and analogs thereof and can be represented by the following structure:

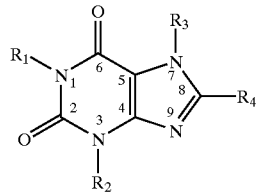

$R_1$ and $R_2$, independently, can be hydrogen or a $C_1–C_6$ linear or branched alkyl optionally interrupted by a carbonyl. $C_1–C_6$ alkyl includes linear or branched species and further includes species that are interrupted in the chain by a carbonyl group, e.g., 5-oxohexyl. $C_1–C_6$ alkyl includes, but is not limited to, methyl, ethyl, n-propyl, isopropyl, n-butyl, isobutyl, sec-butyl and t-butyl. Dyphylline-type compounds with large nonpolar substituents at $R_1$ and $R_2$ usually display an enhancement in both the ability to inhibit cyclic nucleotide phosphodiesterases and to antagonize receptor-mediated actions of adenosine. Preferably, $R_1$ and $R_2$ are methyl.

$R_3$ can be a $C_1–C8$ alkyl (preferably a $C_1–C_4$ alkyl) substituted by one or more moieties selected from the group consisting of a hydroxyl, amino, mercapto, dioxolan, carbonyl, and mixtures thereof. $C_1–C_8$ alkyl includes both linear and branched species, including methyl, ethyl, n-propyl, isopropyl, n-butyl, isobutyl, sec-butyl, t-butyl, n-pentyl, isopentyl, neopentyl, n-hexyl, and the like. Examples of suitable substituted alkyl groups include hydroxymethyl, hydroxyethyl, hydroxypropyl, dihydroxypropyl, e.g., 2,3-dihydroxypropyl or 1,3-dihydroxypropyl, 1,3-dioxolan-2-ylmethyl, methanamino, ethanamino, pyrrolidinomethyl, morpholinomethyl, piperidinomethyl, methanethio, ethanethio, and the like. In a preferred embodiment, $R_3$ is dihydroxypropyl. In a most preferred embodiment, $R_3$ is 2,3-dihydroxypropyl.

R4 can be hydrogen; a substituted or unsubstituted aromatic member; or a cycloalkyl, such as cyclohexyl or cyclopentyl. Addition of an aromatic member or a cycloalkyl at $R_4$ usually markedly increases the affinity of the dyphylline-type compound for adenosine receptors, but reduces inhibition of cyclic nucleotide phosphodiesterases. Suitable aromatic members include phenyl, biphenyl, benzyl, and furyl. Suitable substituents on the aromatic ring include $C_1-C_4$ alkyl, $C_1-C_4$ haloalkyl, $C_1-C_4$ alkoxy, $C_1-C_4$ alkylthio, halo and nitro. $C_1-C_4$ alkyl includes both linear and branched species, including methyl, ethyl, n-propyl, isopropyl, cyclopropyl, n-butyl, isobutyl, sec-butyl, t-butyl, and the like. $C_1-C_4$ haloalkyl includes both linear and branched species of $C_1-C_4$ alkyl, substituted with chloro, fluoro, bromo and iodo, preferably chloro. $C_1-C_4$ alkoxy includes linear or branched species, including, but not limited to, methoxy, ethoxy, n-propoxy, isopropoxy, n-butoxy, isobutoxy, sec-butoxy, t-butoxy, preferably methoxy. $C_1-C_4$ alkylthio includes linear or branched species of $C_1-C_4$ alkyl, substituted with at least one divalent thio (—S—) grouping including: methylthio, ethylthio, isopropylthio, n-butylthio, and the like. Halo includes chloro, fluoro, bromo, iodo, preferably chloro.

Examples of dyphylline-type compounds include:

7-(2,3-dihydroxypropyl)theophylline (also called dyphylline);

7-(β-hydroxyethyl)theophylline;

7-(pyrrolidinomethyl)theophylline;

7-(2-hydroxypropyl)theophylline;

7-(morpholinomethyl)theophylline;

7-(β-hydroxypropyl)theophylline;

7-(piperidinomethyl)theophylline;

7-[2-(diethylamino)ethyl] theophylline (also called metescufylline);

7-(1,3-dioxolan-2-ylmethyl)theophylline (also called doxofylline);

theophylline-7-acetate (also called acefylline); and 1-(5-oxohexyl)-3,7-dimethylxanthine (also called pentoxyfylline).

The preferred compounds are pentoxyfylline and dyphylline. Pentoxyfylline is water soluble and excretion is almost totally urinary. The main biotransformation product is metabolite V (1-(3-carboxypropyl)-3,7-dimethylxanthine). The most preferred compound is dyphylline.

Dyphylline-type compounds are either commercially available or can be synthesized by methods known to those skilled in the art. For example, a method of preparing dyphylline can be found in U.S. Pat. No. 2,575,344, the disclosure of which is incorporated herein by reference.

Also included within the scope of this invention are pharmaceutically acceptable salts of the dyphylline-type compounds shown above. The salts are acid addition salts and can be formed where a basic group is present on the dyphylline-type compound. Where a basic substituent is present, suitable acids for salt formation include, but are not limited to, hydrochloric, sulfuric, phosphoric, acetic, citric, oxalic, malonic, salicylic, malic, gluconic, fumaric, succinic, ascorbic, maleic, and methanesulfonic. The salts are prepared by contacting the dyphylline-type compound with a sufficient amount of the desired acid to produce a salt. The dyphylline-type compound may be regenerated by treating the salt form with a base. The salt forms differ from the dyphylline-type compounds in certain physical properties such as solubility in polar solvents, but the salts are otherwise equivalent for purposes of this invention.

The compounds of the invention can exist in unsolvated as well as solvated forms, including hydrated forms. In general, the solvated forms, including hydrated forms are equivalent to the unsolvated forms for the purposes of this invention.

Method of Treatment

Dyphylline-type compounds are particularly well suited for clinical use in the symptomatic treatment of benign prostatic hyperplasia due to the functional uroselectivity of these compounds. As used herein, uroselective means that the dyphylline-type compounds used in the method of the invention preferentially affect the smooth muscle tone of the prostate as compared to other physiological functions. Functional uroselectivity thus means that the dyphylline-type compounds preferentially act on the lower urinary tract rather than the vasculature or the central nervous system.

Whereas a dose of theophylline is generally metabolized by the liver before being excreted in the urine (only about 10% is unchanged), a dose of a dyphylline-type compound is excreted mostly unchanged in the urine (about 83+/−5% is unchanged). Thus, theophylline is present in urine in very low concentrations. In contrast, dyphylline-type compounds undergo rapid and immediate renal excretion and are found at very high concentrations in the urine. Due to their high concentration in urine, dyphylline-type compounds relax bladder smooth muscle at a much lower blood and systemic levels than theophylline. Furthermore, dyphylline-type compound pharmacokinetics and plasma levels are not influenced by various factors that affect liver function and hepatic enzyme activity, such as smoking, age, congestive heart failure, or concomitant use of drugs which affect liver function.

According to the invention, dyphylline reduces symptoms associated with benign prostatic hyperplasia, including urinary retention, renal failure, bladder decompensation (incontinence), recurrent urinary tract infections and progressive voiding symptoms. The superior efficacy of the dyphylline-type compounds used in the method of the invention (as compared to other methylxanthines) is surprising. Generally, derivatives of methylxanthines which contain substituents at position 7 show a significant reduction in activity. For example, dyphylline doses of about 5 to 6 times theophylline doses are required to produce equivalent bronchodilator response. Lawyer et al., *J. Allergy& Clin. Immunol.* 65:353–357 (1980).

According to the invention, dyphylline-type compounds can be administered to effectively reduce symptoms associated with benign prostatic hyperplasia, including urinary retention, renal failure, bladder decompensation (incontinence), recurrent urinary tract infections and progressive voiding symptoms with less toxic effects than theophylline. As used herein, "toxic effects" refer to adverse effects commonly induced by high plasma concentrations of theophylline, including reduced blood pressure, restlessness, touch sensitivity, nausea, headache, tremors, convulsions, ventricular arrhythmias, seizures and death.

The symptoms of benign prostatic hyperplasia are partially caused by an increase prostatic smooth muscle tone. Dyphylline-type compounds relax bladder smooth muscle and thus relieve involuntary bladder spasms. Dyphylline also relaxes prostatic smooth muscle and increases urine flow through the hypertrophied prostate, thus relieving prostatism and the symptoms thereof. Although not wishing to be bound by theory, it is believed that the superior efficacy of dyphylline-type compounds is due to their high concentration in urine. Dyphylline-type compounds thus have a much lower blood level and systemic level than theophylline, and avoid the serious and unacceptable systemic toxicity of theophylline Combination Therapy The dyphylline-type compounds can be administered in combination with known medical treatments for BPH, such as androgen deprivation therapy, 5α-reductase inhibitors and α-adrenergic antagonist drugs. 5α-reductase inhibitors are compounds that inhibit the action of type 2 5α-reductase, an enzyme that catalyzes the conversion of testosterone to dihydrotestosterone in most androgen sensitive tissues. Finasteride [N-(2-methyl-2-propyl)3-oxo-4-aza-5α-androst-1-ene-17β-carboxamide] is a known 5α-reductase inhibitor. α-Adrenergic-antagonist drugs block adrenergic receptors in hyperplastic prostatic tissue, the prostatic capsule, and the bladder neck, to decrease smooth muscle tone of these structures. A variety of α-adrenergic antagonists are used in the treatment of BPH. Nonselective drugs include phenoxybenzamine and thymoxamnine. Short acting selective drugs include alfuzosin, indoramin and prazosin. Long acting selective drugs including doxazosin, terazosin and tamsulosin. Combination therapy shows synergy in producing both acute and chronic relief.

Finasteride is available from Merck & Co. under the tradename PROSCAR®. It slowly forms a stable enzyme complex with 5α-reductase, thus inhibiting the activity of 5α-reductase. Turnover from the enzyme complex is extremely slow ($t_{1/2}$~30 days). Generally, Finasteride is administered in a single 5 mg once a day. Typically, Finasteride is administered orally.

Phenoxybenzamine is a haloalkylamine that blocks $\alpha_1$- and $\alpha_2$-adrenergic receptors irreversibly. Phenoxybenzamine hydrochloride is available from SmithKline Beecham Pharmaceuticals under the tradename DIBENZYLINE®. While the half life when orally administered is unknown, the half life when administered intravenously is approximately 24 hours. Typically, 10 to 20 mg is administered twice a day.

Prazosin contains a piperazinyl quinazoline nucleus and is a very potent and selective $\alpha_1$-antagonist. Prazosin is well absorbed after oral administration, and bioavailability is about 50% to 70%. Peak concentrations of prazosin in plasma are generally reached 1 to 3 hours after an oral dose. The plasma half life is approximately 2 to 3 hours, and the duration of action is approximately 4 to 6 hours. Dosage ranges from 1 mg 2 to 3 times a day to 20 mg 2 to 3 times a day.

Terazosin is a close structural analog of prazosin. Although it is less potent than prazosin, it is more water soluble than prazoin and has a bioavailability greater than 90%. The half-time elimination of terazosin is approximately 12 hours and its duration of action may extend beyond 18 hours. Thus the drug is generally taken once daily. Generally, 1 to 10 mg are administered once a day.

Doxazosin is another structural analog of prazosin. The half-life of doxazosin is 10 to 20 hours and its duration of action may extend to 36 hours. The bioavailability is about 50% to 70%.

Indoramin is a selective, competitive $\alpha_1$ antagonist. The elimination half life is about 5 hours. The bioavailability of indoramin is generally less than 30% with considerable variability.

Alfuzosin is a quinazoline derivative that is a competitive, selective $\alpha_1$-adrenergic antagonist. There is evidence that this compound might exhibit some selectivity for urethral rather than vascular $\alpha_1$-adrenergic receptors. The elimination of the drug is largely by metabolism. The parent compound has a half-life of about 5 hours.

Formulations

The dyphylline-type compounds can be administered in a wide variety of oral, intravenous and intramuscular dosage forms, preferably the dyphylline-type compound is administered orally, most preferably the dyphylline-type compound is administered orally in a sustained release formulation. It will be obvious to those skilled in the art that the dosage forms may comprise as the active component, either a dyphylline-type compound or a corresponding pharmaceutically acceptable salt thereof. The formulations of the invention further comprise a pharmacologically acceptable carrier. As used herein, "pharmacologically acceptable" means that the carrier is compatible with the other ingredients of the formulations and not deleterious to the recipient.

Pharmaceutically acceptable carriers are known to those of skill in the art and include both solid or liquid carriers. Preferably, the dyphylline-type compound is prepared in a sustained release solid preparation. Solid preparations include powders, tablets, dispersible granules, capsules, and cachets. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet, the active compound is mixed with carrier having the necessary binding properties in suitable proportions and compacted in the shape and size desired. The powders and tablets preferably contain from 5 to 10 to about 80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Alternately, the dyphylline-type compound can be included in a liquid preparation. Liquid preparations include solutions, suspensions and emulsions. For example, water or water-propylene glycol solutions for parenteral injection. Such solutions are prepare so as to be acceptable to biological systems (isotonicity, pH, etc.). Liquid preparations can also be formulated in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing finely divided active component in water with viscous material, i.e., natural or synthetic gums, resins, methyl cellulose, sodium carboxymethyl cellulose, and other well-known suspending agents.

For medical use, the amount of dyphylline-type compound or pharmacologically acceptable salt thereof required to achieve a therapeutic effect will vary with the particular compound and the route of administration. The half-life of dyphylline-type compounds in normal adults is from about 2 to about 3 hours, and total body clearance is about 150 to 200 ml/kg-hr, although renal clearance can be reduced in patients with impaired renal function. Due to the relatively brief half-life in humans, dyphylline-type compounds must be given frequently or in high doses to achieve clinical utility. Alternately, the dyphylline-type compound can be administered in a sustained release formulation.

A suitable dose of a dyphylline-type compound or pharmacologically acceptable salt thereof is about 200 mg to about 2500 mg, administered every 4 to 6 hours, more preferably, about 15 mg/kg, administered orally about every 6 hours. Preferably, the dyphylline-type compound is administered in a sustained release formulation as a tablet or capsule. Preferably, the dyphylline-type compound is administered in a sustained release formulation that releases about 90% to about 100% of the dyphylline-type compound over a twelve hour period.

Sustained release formulations and methods of preparing them are known to those of skill in the art. Generally, a sustained release formulation is a preparation that releases the active component over a desired period of time after administration. Typically, a sustained release formulation is prepared by applying a biodegradable, bioerodible or bioabsorbable polymeric formulation that is biocompatible on the surface of the active component. Examples of polymeric formulations for sustained release formulations include, but are not limited to, hydroxypropylmethylcellulose (HPMC), hydrogenated vegetable oil (HVO), and ethylcellulose.

The term "biodegradable" means that the polymeric formulation degrades over time by the action of enzymes, by hydrolytic action and/or by other similar mechanisms in the human body. By "bioerodible," it is meant that the polymeric formulation erodes or degrades over time due, at least in part, to contact with substances found in the surrounding tissue fluids or cellular action. By "bioabsorbable," it is meant that the polymeric formulation is broken down and absorbed within the human body, for example, by a cell or tissue. "Biocompatible" means that the polymeric formulation does not cause substantial tissue irritation or necrosis.

The formulations may conveniently be presented in unit dosage form and may be prepared by any of the methods well-known in the art of pharmacy. In unit dosage form, the preparation is subdivided into unit doses containing appropriate quantities of the active component. The unit dosage form can be a packaged preparation, the package containing discrete quantities of preparation, for example, packeted tablets, capsules, or powders in vials or ampoules. The unit dosage form can also be a capsule, cachet, tablet itself or it can be the appropriate number of any of these packaged forms.

The invention also includes formulations of a dyphylline-type compound and an α-adrenergic antagonist and/or a 5α-reductase inhibitor. For a composition which includes a dyphylline-type compound and a nonselective α-adrenergic antagonist, a short acting selective α-adrenergic antagonist, or a 5α-reductase inhibitor, it is preferred that the entire composition be prepared in a sustained release formulation. However, in a composition which includes a dyphylline-type compound and a long-acting α-adrenergic antagonist, it is preferred that the dyphylline-type compound be prepared in a sustained release formulation and the long-acting α-adrenergic antagonist be prepared in a quick release formulation. The following examples illustrate formulations suitable for use in the method of the invention.

EXAMPLES

Example 1

A polygel tablet sustained release formulation for use in the method of the invention is prepared by spraying a povidone/water solution onto a mixture of dyphylline and hydroxypropylmethylcellulose (HPMC) in a fluid bed. The material in the fluid bed is then dried and passed through a mill for sizing. Silicon dioxide and magnesium stearate are combined with the dried material, which is then compressed into tablet form. The percentage of each constituent in the formulation and milligrams per tablet are shown in Table 1, below. The polygel tablet provides 90–100% delivery of dyphylline at 12 hours.

TABLE 1

Polygel Tablet, 12 hour Dyphylline

| MATERIAL | PERCENT | MG/TABLET |
|---|---|---|
| Dyphylline | 75.5 | 400 |
| Hydroxypropylmethylcellulose, USP | 18.0 | 95 |
| Povidone, USP | 6.0 | 32 |
| Silicon Dioxide, NF | 0.3 | 2 |
| Magnesium Stearate, NF | 0.2 | 1 |
| Total | 100.0 | 530 |

Example 2

A sustained release hydrogenated vegetable oil (HVO) tablet for use in the method of the invention is prepared by spraying melted vegetable oil onto dyphylline and allowing the oil to cool. Silicon dioxide and magnesium stearate are then combined with the dyphilline/oil mixture, which is then compressed into tablet form. The percentage of each constituent in the formulation and milligrams per tablet are shown in Table 2, below. The HVO tablet provides 90–100% delivery of dyphylline at 12 hours.

TABLE 2

HVO Tablet, 12 hour Dyphylline

| MATERIAL | PERCENT | MG/TABLET |
|---|---|---|
| Dyphylline | 73.0 | 400 |
| Hydrogenated Vegetable Oil, NF | 26.0 | 142 |
| Silicon Dioxide, NF | 0.3 | 2 |
| Magnesium Stearate, NF | 0.7 | 4 |
| Total | 100.0 | 548 |

Example 3

A sustained release formulation of solvent coated beads for use in the method of the invention is prepared by spraying an ethylcellulose/solvent solution onto dyphilline in a fluid bed. The material in the fluid bed is dried and passed through a screen for sizing. Microcrystalline cellulose, silicon dioxide and magnesium stearate are combined with the material, which is then compressed into tablet form. The percentage of each constituent in the formulation and milligrams per tablet are shown in Table 3, below. The tablet provides 90–100% delivery of dyphylline at 12 hours.

TABLE 3

Solvent Coated Beads-Tablet, 12 hour Dyphylline

| MATERIAL | PERCENT | MG/TABLET |
|---|---|---|
| Dyphylline | 71.1 | 400 |
| Ethylcellulose, USP | 19.0 | 107 |

TABLE 3-continued

Solvent Coated Beads-Tablet, 12 hour Dyphylline

| MATERIAL | PERCENT | MG/TABLET |
| --- | --- | --- |
| Microcrystalline Cellulose, NF | 9.0 | 51 |
| Croscarmellose Sodium, NF | 0.5 | 3 |
| Sorbitan Monooleate, NF | 0.4 | 2 |
| Total | 100.0 | 563 |

Example 4

A sustained release formulation for the method of the invention is prepared by spraying an ethylcellulose/solvent solution onto dyphilline in a fluid bed. The material in the fluid bed is dried and passed through a screen for sizing. Sorbitan monooleate and magnesium stearate are combined with the material, which is then filled into a capsule. The percentage of each constituent in the formulation and milligrams per capsule are shown in Table 4, below. The capsule provides 90–100% delivery of dyphylline at 12 hours.

TABLE 4

Solvent Coated Beads Capsule, 12 hour Dyphylline

| MATERIAL | PERCENT | MG/CAPSULE |
| --- | --- | --- |
| Dyphylline | 78.4 | 400 |
| Ethylcellulose, USP | 21.0 | 107 |
| Sorbitan Monooleate, NF | 0.4 | 2 |
| Magnesium Stearate, NF | 0.2 | 1 |
| Total | 100.0 | 510 |

Example 5

A polygel tablet containing dyphylline and prazosin is prepared by spraying a povidone/water solution onto dyphylline, prazosin and hydroxypropylmethylcellulose (HPMC) in a fluid bed. The material in the fluid bed is dried and passed through a mill for sizing. Silicon dioxide and magnesium stearate are combined with the material, which is then compressed into a tablet form. The percentage of each constituent in the formulation and milligrams per tablet are shown in Table 5, below. The tablet provides 90–100% delivery of dyphylline and prazosin at 12 hours.

TABLE 5

Polygel Tablet, 12 Hour Dyphylline and Prazosin

| MATERIAL | PERCENT | MG/TABLET |
| --- | --- | --- |
| Dyphylline | 74.5 | 400 |
| Prazosin HCl | 0.9 | 5 |
| Hydroxypropylmethylcellulose, USP | 18.0 | 97 |
| Povidone, USP | 6.0 | 32 |
| Silicon Dioxide, NF | 0.3 | 2 |
| Magnesium Stearate, NF | 0.2 | 1 |
| Total | 100.0 | 537 |

Example 6

A sustained release hydrogenated vegetable oil (HVO) tablet containing dyphylline and prazosin is prepared by spraying melted vegetable oil onto dyphylline and prazosin and allowing the oil to cool. Silicon dioxide and magnesium stearate are combined with the dyphylline/prazosin/oil material, which material is then compressed into a tablet. The percentage of each constituent in the formulation and milligrams per 530 milligram tablet are shown in Table 6, below. The tablet provides 90–100% delivery of dyphylline and prazosin at 12 hours.

TABLE 2

Hydrogenated Vegetable Oil (HVO) Tablet, 12 hour Dyphylline and Prazosin

| MATERIAL | PERCENT | MG/TABLET |
| --- | --- | --- |
| Dyphylline | 72.1 | 400 |
| Prazosin HCl | 0.9 | 5 |
| Hydrogenated Vegetable Oil, NF | 26.0 | 144 |
| Silicon Dioxide, NF | 0.3 | 2 |
| Magnesium Stearate, NF | 0.7 | 4 |
| Total | 100.0 | 555 |

Example 7

A sustained release formulation of solvent coated beads is prepared by spraying an ethylcellulose/solvent solution onto dyphilline and prazosin in a fluid bed. The material in the fluid bed is dried and passed through a screen for sizing. Microcrystalline cellulose, silicon dioxide and magnesium stearate are combined with the material, which material is then compressed into a tablet. The percentage of each constituent in the formulation and milligrams per tablet are shown in Table 7, below. The tablet provides 90–100% delivery of dyphylline and prazosin at 12 hours.

TABLE 7

Solvent Coated Beads-Tablet, 12 Hour Dyphylline and Prazosin

| MATERIAL | PERCENT | MG/TABLET |
| --- | --- | --- |
| Dyphylline | 70.2 | 400 |
| Prazosin HCl | 0.9 | 5 |
| Ethylcellulose, USP | 19.0 | 109 |
| Microcrystalline Cellulose, NF | 9.0 | 51 |
| Croscarmellose Sodium, NF | 0.5 | 3 |
| Sorbitan Monooleate, NF | 0.4 | 2 |
| Total | 100.0 | 570 |

Example 8

A sustained release formulation of solvent coated beads is prepared by spraying an ethylcellulose/solvent solution onto dyphilline and prazosin in a fluid bed. The material in the fluid bed is dried and passed through a screen for sizing. Sorbitan monooleate and magnesium stearate are combined with the material, which is then filled into a capsule. The percentage of each constituent in the formulation and milligrams per tablet are shown in Table 8, below. The capsule provides 90–100% delivery of dyphylline and prazosin at 12 hours.

TABLE 8

Solvent Coated Beads Capsule, 12 hour dyphylline and prazosin

| MATERIAL | PERCENT | MG/CAPSULE |
| --- | --- | --- |
| Dyphylline | 77.4 | 400 |
| Prazosin HCl | 1.0 | 5 |
| Ethylcellulose, USP | 21.0 | 108 |
| Sorbitan Monooleate, NF | 0.4 | 2 |

TABLE 8-continued

Solvent Coated Beads Capsule, 12 hour dyphylline and prazosin

| MATERIAL | PERCENT | MG/CAPSULE |
|---|---|---|
| Magnesium Stearate, NF | 0.2 | 1 |
| Total | 100.0 | 517 |

Example 9

A first layer of a formulation for sustained release of dyphylline and instant release of doxazosin is prepared by spraying a povidone/water solution onto dyphilline and HPMC in a fluid bed. The material in the fluid bed is dried and passed through a mill for sizing. Silicon dioxide and magnesium stearate are combined with the material to form the first layer of the formulation. The percentage of each constituent in the formulation in the first layer and milligrams per tablet are shown in Table 9, below.

TABLE 9

Polygel 12 Hr. Dyphylline

| MATERIAL, 1st LAYER | PERCENT | MG/TABLET |
|---|---|---|
| Dyphylline | 75.5 | 400 |
| Hydroxypropylmethylcellulose, USP | 18.0 | 95 |
| Povidone, USP | 6.0 | 32 |
| Silicon Dioxide, NF | 0.3 | 2 |
| Magnesium Stearate, NF | 0.2 | 1 |
| Total | 100.0 | 530 |

A second layer of a formulation for sustained release of dyphylline and instant release of doxazosin is prepared by mixing doxazosin, microcrystalline cellulose and calcium phosphate. Vegetable oil and magnesium stearate are then combined with the doxazosin/cellulose/calcium phosphate mixture. The percentage of each constituent in the formulation and milligrams per tablet are shown in Table 10, below. The final mixture is then compressed with the first layer. The bilayer tablet provides 90–100% delivery of dyphylline at 12 hours and instant release of doxazosin.

TABLE 10

IR Doxazosin

| MATERIAL, 2nd LAYER | PERCENT | MG/TABLET |
|---|---|---|
| Doxazosin Mesylate | 3.5 | 4 |
| Microcrystalline Cellulose, NF | 42.0 | 48 |
| Calcium Phosphate, Bibasic, Dihydrate, NF | 50.0 | 57 |
| Hydrogenated Vegetable Oil, NF | 4.0 | 5 |
| Magnesium Stearate, NF | 0.5 | 1 |
| Total | 100.0 | 114 |

Example 10

A first layer of a formulation for sustained release of dyphylline and instant release of doxazosin is prepared by spraying an ethylcellulose/solvent solution onto dyphylline in a fluid bed. The material in the fluid bed is dried and passed through a screen for sizing. Microcrystalline cellulose, croscarmellose sodium and sorbitan monooleate are combined with the material to form the first layer of the formulation. The percentage of each constituent in the first layer of the formulation in milligrams per tablet are shown in Table 11, below.

TABLE 11

Solvent Coated Beads, 12 hour Dyphylline

| MATERIAL, | PERCENT | MG/TABLET |
|---|---|---|
| Dyphylline | 71.1 | 400 |
| Ethylcellulose, USP | 19.0 | 107 |
| Microcrystalline Cellulose, NF | 9.0 | 51 |
| Croscarmellose Sodium, NF | 0.5 | 3 |
| Sorbitan Monooleate, NF | 0.4 | 2 |
| Total | 100.0 | 563 |

A second layer of the formulation for sustained release of dyphylline and instant release of doxazosin is prepared by mixing doxazosin, microcrystalline cellulose and calcium phosphate. Vegetable oil and magnesium stearate are then combined with the doxazosin/cellulose/calcium phosphate mixture. The percentage of each constituent in the formulation and milligrams per tablet are shown in Table 12, below. The final mixture is then compressed with the first layer. The solvent coated beads provide 90–100% delivery of dyphylline at 12 hours and instant release of doxazosin.

TABLE 12

IR Doxazosin

| MATERIAL, 2nd LAYER | PERCENT | MG/TABLET |
|---|---|---|
| Doxazosin Mesylate | 3.5 | 4 |
| Microcrystalline Cellulose, NF | 42.0 | 48 |
| Calcium Phosphate, Bibasic, Dihydrate, NF | 50.0 | 57 |
| Hydrogenated Vegetable Oil, NF | 4.0 | 5 |
| Magnesium Stearate, NF | 0.5 | 1 |
| Total | 100.0 | 114 |

Example 11

A formulation of dyphylline and doxazosin is prepared by spraying an ethylcellulose/solvent solution onto dyphylline in a fluid bed. The material in the fluid bed is dried and passed through a screen for sizing. Doxazosin, sorbitan monooleate, and magnesium stearate are combined with the material.

TABLE 13

Solvent Coated Beads Capsule, 12 hour Dyphylline, IR Doxazosin

| MATERIAL, 1st LAYER | PERCENT | MG/CAPSULE |
|---|---|---|
| Dyphylline | 79.6 | 400 |
| Doxazosin Mesylate | 0.8 | 4 |
| Ethylcellulose, USP | 19.0 | 96 |
| Sorbitan Monooleate, NF | 0.4 | 2 |
| Magnesium Stearate, NF | 0.2 | 1 |
| Total | 100.0 | 503 |

All patents, patent applications, and publications cited herein are hereby incorporated by reference as if individually incorporated. It is to be understood that the above description is intended to be illustrative, and not restrictive. Various modifications and alterations of this invention will become apparent to those skilled in the art from the foregoing description without departing from the scope and the spirit of this invention, and it should be understood that this invention is not to be unduly limited to the illustrative embodiments set forth herein.

What is claimed is:

1. A method of symptomatic treatment of benign prostatic hyperplasia in a subject, comprising: administering to a subject in need thereof, an effective amount of a compound of the formula:

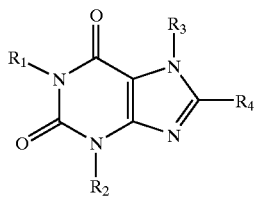

wherein $R_1$ and $R_2$, independently, are hydrogen or a $C_1$–$C_6$ linear or branched alkyl optionally interrupted by a carbonyl;

$R_3$ is a $C_1$–$C_8$ alkyl substituted by one or more moieties selected from the group consisting of hydroxyl, amino, mercapto, dioxolan, carbonyl and mixtures thereof; and $R_4$ is hydrogen; a substituted or unsubstituted aromatic member selected from the group consisting of phenyl, biphenyl, benzyl, and furyl, wherein the substituent is selected from the group consisting of $C_1$–$C_4$ alkyl, $C_1$–$C_4$ haloalkyl, $C_1$–$C_4$ alkoxy, $C_1$–$C_4$ alkylthio, halo and nitro; or a cycloalkyl selected from the group consisting of cyclohexyl and cyclopentyl; or a pharmaceutically acceptable acid addition salt thereof, in a unit dosage form.

2. The method of claim 1, wherein $R_1$ and $R_2$ are methyl.

3. The method of claim 1, wherein $R_3$ is a $C_1$–$C_8$ alkyl substituted by one or more hydroxyl groups.

4. The method of claim 1, wherein $R_4$ is a substituted or unsubstituted aromatic member selected from group consisting of phenyl, and benzyl, and wherein the substituent is selected from the group consisting of $C_1$–$C_4$ alkyl, $C_1$–$C_4$ haloalkyl, $C_1$–$C_4$ alkoxy, $C_1$–$C_4$ alkylthio, halo and nitro.

5. The method of claim 1, wherein $R_1$ and $R_2$ are methyl; $R_3$ is a $C_1$–$C_4$ alkyl substituted by one or more hydroxyl groups; and $R_4$ is hydrogen.

6. The method of claim 1, wherein $R_1$ and $R_2$ are methyl; $R_3$ is dihydroxypropyl; and $R_4$ is hydrogen.

7. The method of claim 1, wherein $R_1$ and $R_2$ are methyl; $R_3$ is 2,3-dihydroxypropyl; and $R_4$ is hydrogen.

8. The method of claim 1, wherein the compound is administered orally.

9. The method of claim 1, wherein the compound is administered in combination with a pharmaceutically acceptable carrier.

10. The method of claim 1, wherein the compound is administered in a sustained release carrier.

11. The method of claim 1, wherein the compound is administered in combination with an α-adrenergic-antagonist.

12. The method of claim 11, wherein the α-adrenergic-antagonist is a nonselective α-adrenergic-antagonist selected from the group consisting of phenoxybenzamine and thymoxamine.

13. The method of claim 12, wherein the compound and the nonselective α-adrenergic antagonist are administered in a sustained release formulation.

14. The method of claim 11, wherein the α-adrenergic-antagonist is a short acting α-adrenergic-antagonist selected from the group consisting of alfuzosin, indoramin, and prazosin.

15. The method of claim 14, wherein the compound and the short acting α-adrenergic antagonist are administered in a sustained release formulation.

16. The method of claim 11, wherein the α-adrenergic-antagonist is a long acting α-adrenergic-antagonist selected from the group consisting of doxazosin, terazosin and tamsulosin.

17. The method of claim 16, wherein the compound is included in a sustained release formulation and the long acting α-adrenergic antagonist is included in a quick release formulation.

18. The method of claim 1, wherein the compound is administered in combination with a 5α-reductase inhibitor.

19. The method of claim 18, wherein the 5α-reductase inhibitor is finasteride.

20. The method of claim 18, wherein the compound and the 5α-reductase inhibitor are included in a sustained release formulation.

21. The method of claim 1, wherein the compound is administered in combination with a 5α-reductase inhibitor and an α-adrenergic-antagonist.

* * * * *